United States Patent [19]
Dario et al.

[11] Patent Number: 5,906,591
[45] Date of Patent: May 25, 1999

[54] ENDOSCOPIC ROBOT

[75] Inventors: Paolo Dario, Livorno; Maria Chiara Carrozza; Andrea Pietrabissa, both of Pisa; Bernardo Magnani; Lucia Lencioni, both of Livorno, all of Italy

[73] Assignee: Scuola Superiore Di Studi Universitari E Di Perfezionamento S. Anna, Pisa, Italy

[21] Appl. No.: 08/967,306

[22] Filed: Oct. 21, 1997

[30] Foreign Application Priority Data

Oct. 22, 1996 [IT] Italy .................................. MI96A2188

[51] Int. Cl.⁶ .............................. A61M 37/00; A61B 1/22
[52] U.S. Cl. .............................................. 604/95; 600/114
[58] Field of Search .................................. 604/95, 96, 99, 604/280; 600/114, 115, 116, 118, 139, 141

[56] References Cited

U.S. PATENT DOCUMENTS

| | | | |
|---|---|---|---|
| 2,767,705 | 10/1956 | Moore ...................................... | 600/114 |
| 4,176,662 | 12/1979 | Frazer ......................................... | 128/6 |
| 4,676,228 | 6/1987 | Krasner et al. ............................. | 128/4 |
| 5,337,732 | 8/1994 | Grundfest et al. . | |
| 5,398,670 | 3/1995 | Ortiz et al. ............................... | 600/114 |
| 5,454,364 | 10/1995 | Kruger .................................... | 600/114 |

*Primary Examiner*—Wynn Wood Coggins
*Assistant Examiner*—Michael J. Hayes
*Attorney, Agent, or Firm*—Browdy and Neimark

[57] ABSTRACT

An endoscopic robot (1), designed for being inserted into a body cavity (C) of a patient and advanced therein in a prefixed direction (A) with a so-called inchworm-like motion, comprising a variable length segment (2) and aspiration means (12, 13) for selectively producing a pneumatic vacuum (V) between the robot (1) and the body cavity (C) at the robot ends (3, 4) sufficient to produce a substantial anchorage to the body cavity walls, thereby allowing the inchworm-like motion and avoiding, at the same time, any pushing action against the body cavity walls which causes discomfort and pain to the patient.

8 Claims, 3 Drawing Sheets

ENDOSCOPIC ROBOT

FIELD OF THE INVENTION

The present invention relates to an endoscopic robot of the type designed for being inserted in a body cavity or lumen such as, for example, the colon, when carrying out diagnostic or surgical endoscopic procedures and for being moved on a predetermined direction with a so-called inchworm-like motion.

BACKGROUND ART

As is known, endoscopic technique was developed in the medical field with the aim to reduce, as far as it is possible, the necessity of conventional surgical operation in the course of diagnostic procedures, and to limit, at the same time, patient discomfort, recovery time and possible side effects.

To these purposes there are known various endoscopic instruments which are driven directly by the surgeon to advance into the body of the patient. Frequently, body cavities, which said instruments must traverse, are extremely meandering and brittle at the same time, so that from one side a high skill of the surgeon driving the instrument is required, while, from the other side endoscopic diagnostic or surgical procedures are often unfeasible due to the extreme difficulty of performing them. To obviate these inconveniences it has been suggested the use, in endoscopic procedures, of a robot having an autonomous ability to move within the body cavities of a patient and to adapt its configuration to that of the surrounding environment. All necessary surgical and/or diagnostic instruments such as micro-arms, microcameras, and laser emitters can be secured to this type of robot.

Endoscopic robots of the above specified type are known, which, once they are inserted in a body cavity of the patient, move therein with a "snake" or "tentacle" or "elephant trunk" or "inchworm" locomotion mode. These robots have a limited number of degrees of freedom, that is self-bending is allowed in more than one direction with respect to the advancing direction, optionally combined with a rotation about its own axis.

To enable the above mentioned robot to advance in a body cavity of a patient a large amount of air must be blown into the cavity to cause a sufficient widening of it to permit the passage of the robot.

The above advancement mode is painful for the patient as the inspected cavity can be subjected to unnatural expansions. Furthermore, the active means for bending the robot are usually brittle and expensive and increase the size of the robot thereby limiting the possibilities of use.

U.S. Pat. No. 5,337,732 (Grundfest et al.) discloses an endoscopic robot having a redundant number of degrees of freedom and being constituted by a series of mutually articulated rigid segments, designed for being passively bent with respect to one another as a result of the robot locomotion in the cavity. To this purpose the robot has a inchworm-like locomotion mode and anti-slippage means between robot and cavity formed, as an alternative or in combination, by inflatable balloons, blade-like members, protruding and retractable arch members.

The above mentioned anti-slippage means result in a direct interference against the walls of the cavity on which an outwardly pushing action is exerted; the interference may cause an intense pain to the patient as well as a damage to the tissues.

Furthermore the anti-slippage means do not assure a proper durable anchorage to the cavity walls, but only an increased friction due to the force exerted against the walls. For this reason the above endoscopic robot must be equipped with a plurality of anchoring means which, unavoidably, increase its length and, consequently, the discomfort of the patient.

SUMMARY OF THE INVENTION

The technical problem of the present invention is to provide an endoscopic robot suitable to overcome the above mentioned drawbacks of the prior art similar devices.

The problem is solved with an endoscopic robot of the above mentioned type comprising at least a variable length segment extending between a front end and a back end in a predetermined direction and characterized in that it comprises, at each end, respective front and back aspiration means for selectively producing a pneumatic vacuum between the endoscopic robot and the body cavity, sufficient to provide a substantial anchorage through the corresponding end thereby allowing said inchworm-like motion.

The main advantage of the endoscopic robot according to the invention consists in that a firm anchorage is achieved capable of making possible to perform an actual inchworm-like motion, thus substantially avoiding any pushing action against the body cavity walls which cause discomfort and pain to the patient, as well as damages to the biological tissues.

BRIEF DESCRIPTION OF THE DRAWINGS

Further characteristics and advantages of the endoscopic robot according to the invention will be apparent from the description of an embodiment thereof made by way of a not limiting example with reference to the attached drawings in which.

DESCRIPTION OF THE PREFERRED EMBODIMENT

Figure 1:
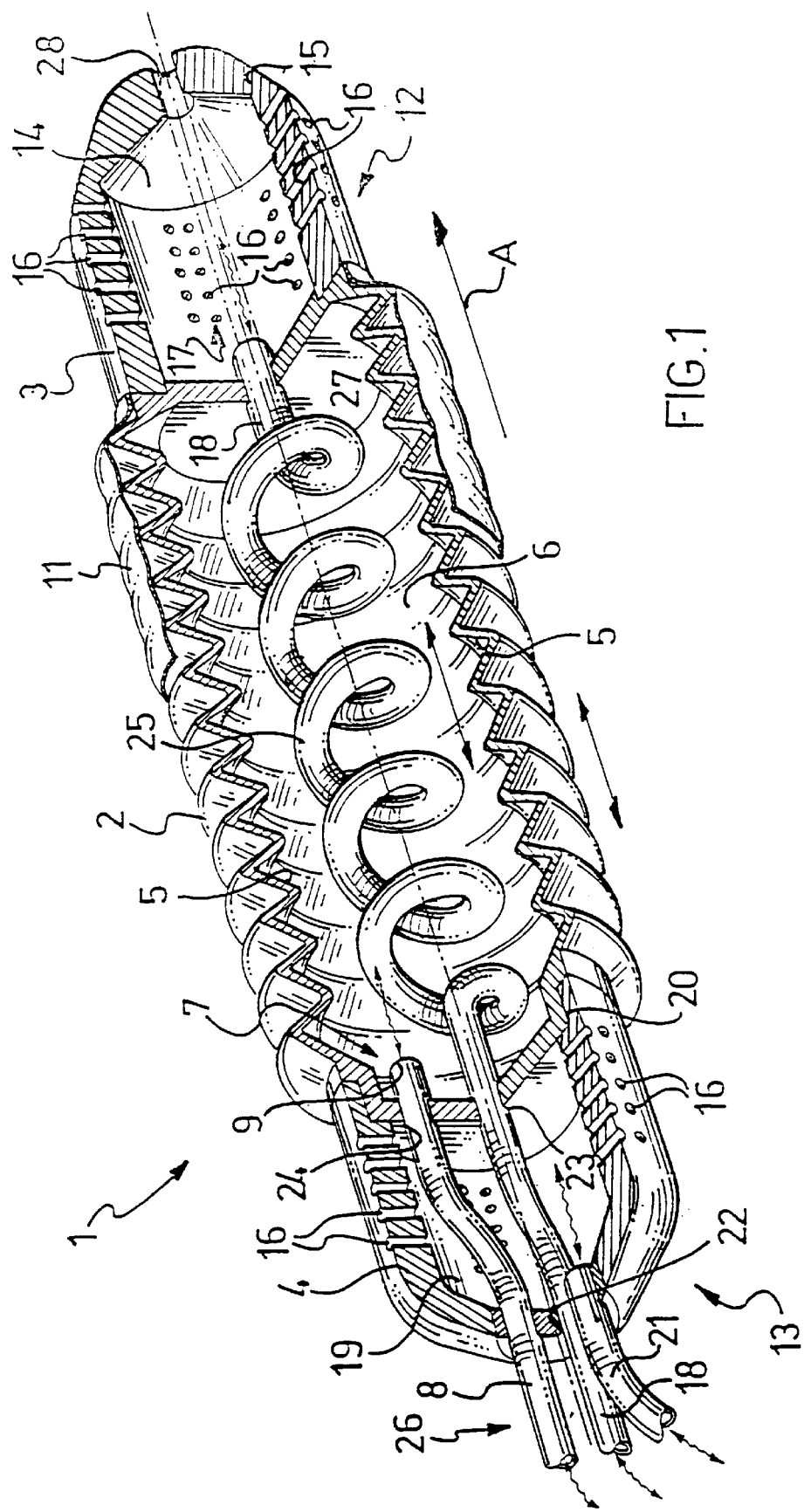
FIG. 1 is a partially segmented, perspective view of an endoscopic robot according to the invention designed for colonscopy.

Turning now to the drawings and in particular to FIG. 1, there is shown an endoscopic robot 1 of the type suitable of being used for endoscopic diagnostic and/or surgical procedures, in combination with suitable instruments not shown, especially designed for these operations such as servomotored micro-arms, microcameras, laser emitters and the like. To this end robot 1 is designed for being inserted into a body cavity C of a patient, i.e. the colon in the present example, and displaced according to a inchworm-like motion, as will be appreciated more clearly hereinafter. Robot 1 has a substantially elongated cylindrical shape and comprises a central variable length segment 2, which is single in the present embodiment, extending between a first and a second end, respectively indicated at 3 and 4, each of them being rounded off to make easier the insertion of the robot into colon C of the patient. Inchworm motion means repetitous alternating sequences of extensions and contractions of variable length segment 2.

Ends 3 and 4 are called front end and back end in accordance to a prefixed advancing direction A during the motion, whether robot 1 is going in or out with respect to body cavity C that, in the present example, is the colon. In the following 3 indicates the front end and 4 the back end, but, unless otherwise specified, the present description will be functionally applicable to each end 3, 4 with respect to the reference direction.

Variable length segment 2 has walls 5 defining an inner chamber 6 containing a fluid, which is air in the present embodiment.

Figure 3:
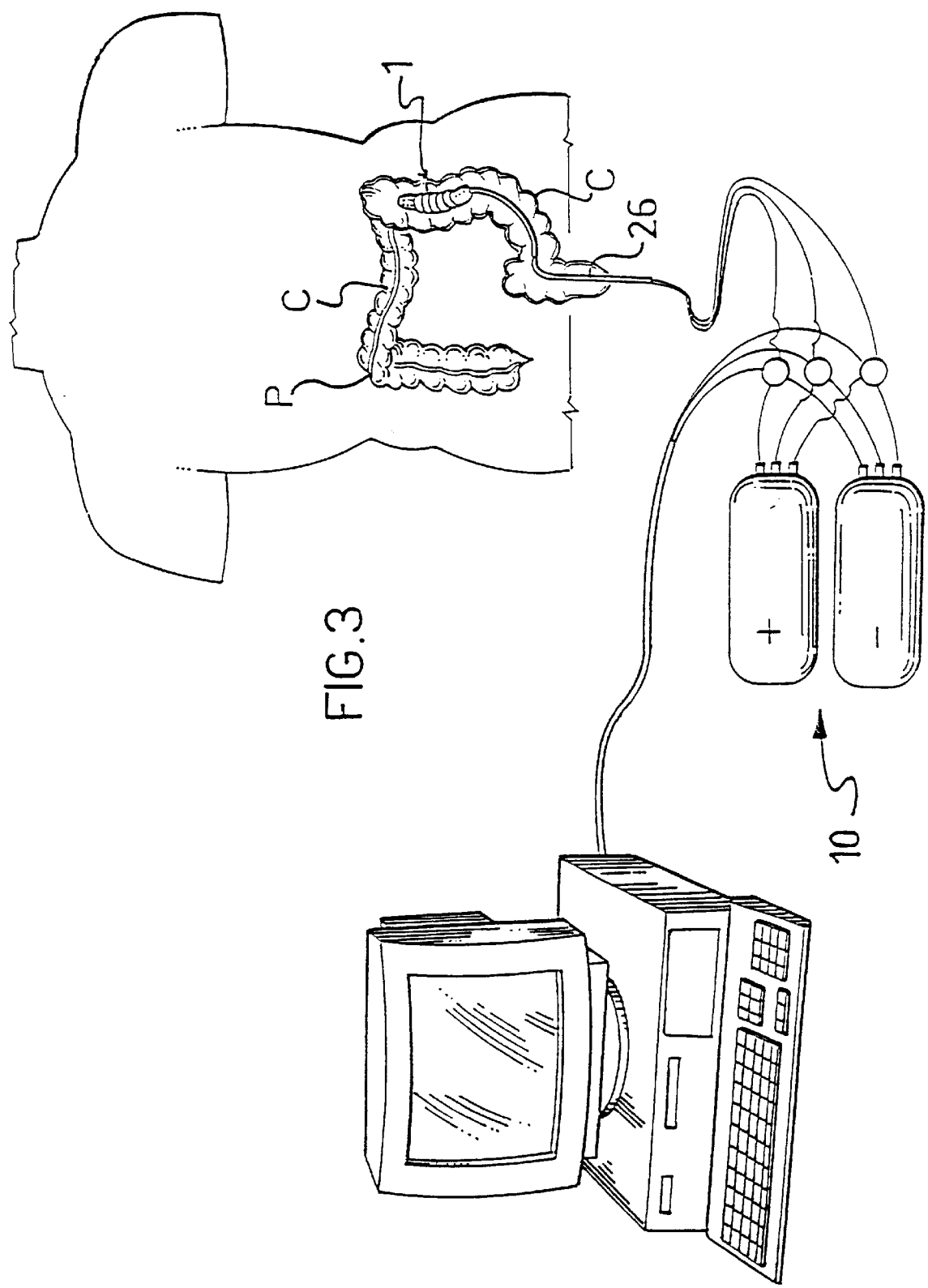
FIG. 3 is a schematic view of the system controlling the endoscopic robot of FIG. 1, while operating within the patient colon.

Walls 5 are made of an elastic and flexible material and have a bellows structure. In this way, segment 2 is elastically deformable and is flexible whereby it can also be bent on itself. Segment 2 comprises means 7 for supplying and aspirating the air to and from chamber 6. Air supplying and aspirating means 7 comprise a flexible conduit 8 passing through second end 4, i.e. the back end in the present description, and has an end 9 opening into chamber 6. Flexible conduit 8 extends between endoscopic robot 1 and a control unit 10 placed outside the patient (FIG. 3) which comprises a control system for supplying and aspirating the air to/from chamber 6. The supplying and aspiration steps occur in an alternating sequence to extend or, respectively, contract variable length segment 2, according to the motion of the so-called inchworm type.

Variable length segment 2 also comprises an elastic and flexible sheath 11 placed on the outside of the elastically deformable, bellows shaped walls. Sheath 11 adheres to walls 5 of segment 2 thus making their surface smoothly sliding along the walls of colon C.

At each end 3, 4 endoscopic robot 1 comprises front and back aspiration means 12 and 13 for producing a selective pneumatic vacuum V (FIGS. 2B–2H), between endoscopic robot 1 and colon C, to substantially secure the corresponding front and/or back end 3, 4 to said colon walls. The aspiration-induced anchorage is such that the actual inchworm-like motion is allowed as the not secured end is free to move in a prefixed direction A, being trailed by repetitous expansions and contractions of segment 2.

Front aspiration means 12 comprise a front chamber 14 formed in the corresponding front end 3, and having rigid walls 15. Walls 15 of front chamber 14 are secured, for example by means of a permanent glueing, to said variable length segment 2 in correspondence to deformable walls 5, so that the front part of segment 2 is sealed up by front chamber 14. Front aspiration means 12 further comprise a plurality of holes 16, passing through rigid walls 15 from chamber 14 to colon walls C and arranged in four groups of rows 17 spaced at an angle of 90° from one another around front end 3. In this way holes 16 are always close to colon walls C along at least a row 17. Front aspiration means 12 further comprise a first aspirating flexible tube 18 for communicating said front chamber to an aspiration equipment placed outside the patient and being part of control unit 10.

Like front aspiration means 12, back aspiration means 13 comprise a back chamber 19, formed in the corresponding back end 4 and symmetrically equal to front chamber 14, having rigid walls 20 secured to said variable length segment 2 which is sealed up by back chamber 19. Back aspiration means 13 further comprise a plurality of through holes 16 arranged in the same way as in the front end 3, and a second aspirating flexible tube 21 communicating rear chamber 19 to the above mentioned aspiration equipment of control unit 10.

The aspiration equipment is designed to induce by aspiration a selective pneumatic vacuum, of moderate degree to not create painful discomfort to the patient while allowing the anchorage of robot 1 and the inchworm-like forward movement.

Holes 16 have a suitable diameter to limit the entry of body fluids in chambers 14, 19, said fluids being anyway disposable through tubes 18, 21.

With reference to the back end 4, a first opening 22 is formed in walls 20 thereof in a central position for entering tubes 8, 21 and flexible conduit 18 in back chamber 19. First flexible tube 18 and flexible conduit 8 cross back chamber 19 longitudinally up to chamber 6, in correspondence to respective second and third opening 23, 24 in walls 20. Chamber 6 of variable length segment 2 is crossed longitudinally by a portion 25 of first flexible tube 18. Portion 25 is in the form of an helical spiral to be elastically deformable so as to adapt to the extensions and contractions of segment 2.

A fourth opening 27 is formed on rigid walls 15 of front chamber 14 in correspondence to chamber 6 to provide a passage for first flexible conduit 18. A further fifth opening 28 is finally formed at the tip of front end 3 in rigid walls 15 to provide a passage, for power supply and control cables connected to surgical and/or diagnostic instruments, not shown, associated to end 3.

Aspirating flexible pipes 18, 21 and flexible conduit 8 form a tail 26 extending from second end 4 connected to endoscopic robot 1 and trailed by the latter while moving through the colon.

With reference to a method for performing the locomotion of an endoscopic robot through a lumen, the operation of endoscopic robot 1 according to the present invention will be described hereunder.

The method comprises a series of advancing cycles, one of which is shown in FIGS. 2A to 2H to be repeated after an accurate control of the position and the configuration of robot 1 by means of known systems.

Figure 2:
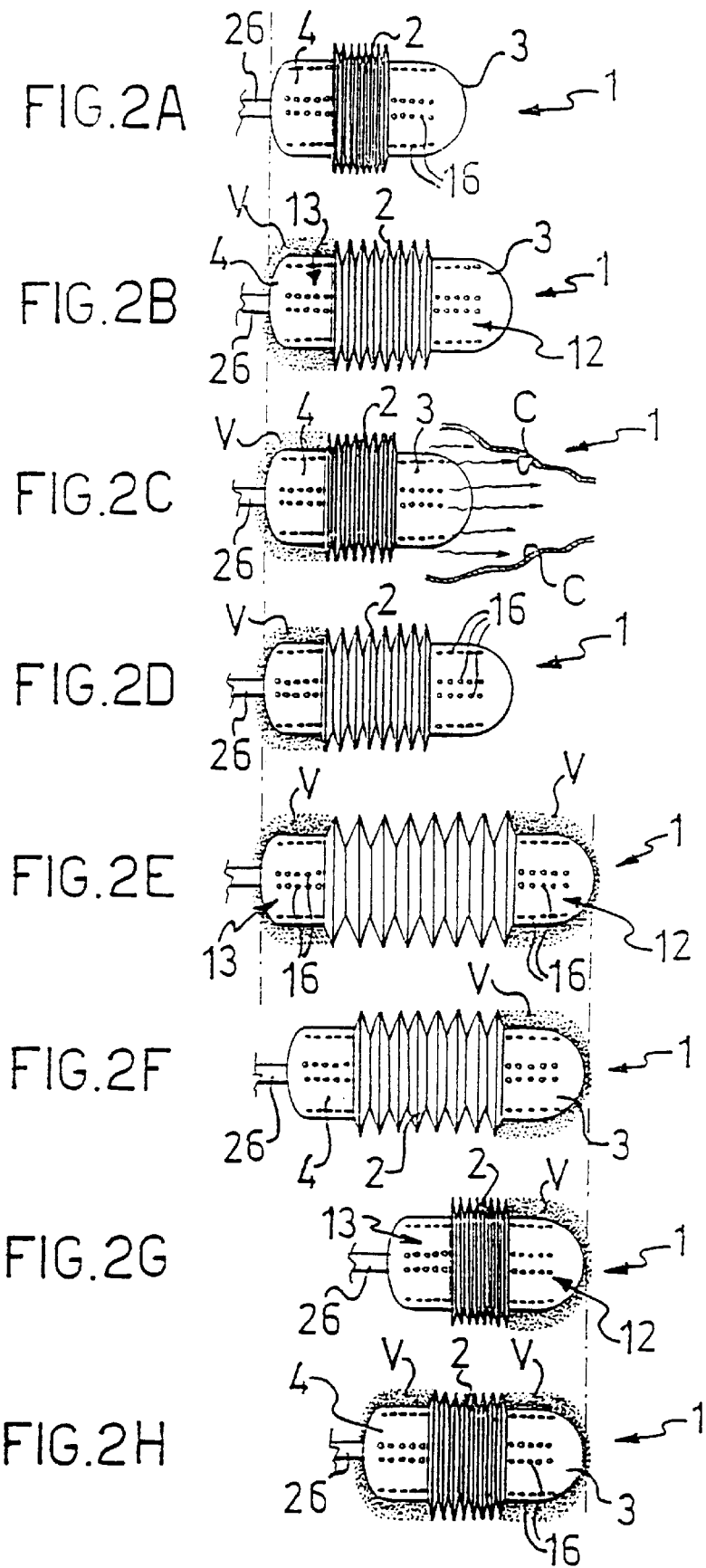
FIGS. 2A, 2B, 2C, 2D, 2E, 2F, 2G and 2H show an advancement cycle of the endoscopic robot of FIG. 1.

In FIG. 2A robot 1 is shown in a substantially contracted position against the walls of the colon after the introduction in the colon C of the patient. The method according to the invention comprises a step in which, starting from the above contracted position, a pneumatic vacuum V is induced by aspiration at the back end 4 of segment 2. The vacuum condition produced in back chamber 19 (FIG. 2B) by means of the aspiration equipment of control unit 10 is such that end 4 is firmly secured against colon walls C due to the induced vacuum. In this condition, if necessary, colon C walls C are spread apart in front of end 3 by flow inversion in first flexible conduit 18. Air is thus blown through holes 16 of front end 3 (FIG. 2C).

The method comprises sequentially a step in which segment 2 is axially expanded from the previous contracted position to an axially expanded or extended position thus causing the forward movement of front end 3 of robot 1 through colon C (FIG. 2D). This, axial expansion is performed against the natural elasticity of bellows segment 2 and is produced by the forced air introduction through flexible conduit 8 into chamber 6 of segment 2.

Afterwards, in the same way as previously done for back end 4, a pneumatic vacuum V is induced by aspiration at front end 3, so as to firmly secure it to colon walls C (FIG. 2E). At this point aspiration at back end 4 is interrupted thus releasing the corresponding pneumatic vacuum V and the relevant anchorage and releasing back end 4 which is free to move in the prefixed direction A (FIG. 2F).

The method then comprises a step consisting in contracting the variable length segment 2 from the extended position to the contracted position, thus actually performing the inchworm-like motion (FIG. 2G) The contraction is due to the forced air aspiration from chamber 6 of segment 2. The elasticity of bellows segment 2 assists in realizing the contraction. At this point a new vacuum V is created by aspiration at the back end 4 (FIG. 2H) to start again with the inchworm-like motion or to reverse the motion.

When the body cavity C to be gone through has a loop P (FIG. 3), robot 1 is able to passively bend as being advanced by the inchworm-like motion thanks to the flexibility of segment 2. The best path is selected by robot 1 thanks to the streamlined profile of ends 3, 4. This feature allows the robot to be driven in a semiautomatic or even automatic fashion, is so far as it is able to reach a predetermined area of the patient's body through a lumen such as the colon, the small intestine, the oesophagus, the urinary tract and the biliary system.

A number of variations can be made to the above described endoscopic robot.

Front and back chambers can be removeably connected to the variable length segment. In this way they can be replaced in case of damage, due for example to an obstruction with polluting matter, or for maintenance.

The variable length segment can be constituted by a smooth cylinder with elastically extensible walls, thus avoiding the use of bellows and the relevant sheath. If special requirements exist due to the diagnostic or surgical instruments, the robot according to the invention may include more than one variable length segment each of them possibly being suitable of an independent drive control.

Air distribution too can be differently performed, for example by using micro-valves placed inside the robot, possibly equipped with actuating devices made of a shape-memory alloy, providing for the control of the aspiration equipment.

The robot can be made of disposable plastic materials provided that they do not negatively affect the good operation of the robot and be suitable for the introduction in a body cavity.

The above mentioned aspiration tubes and the holes can be used not only to produce the pneumatic vacuum, but even to suck liquids or gases from the cavity or to deliver drugs and/or diagnostic substances such as contrast liquids.

The above described robot can be associated to means for detecting its actual position and shape operable in connection with said control unit in, a semi-autonomous or fully autonomous fashion.

In addition to the above mentioned advantage the endoscopic robot according to the invention can be made of an extremely reduced length thanks to the fact that only two anchorage points are required. Furthermore it can be passively bent even performing rotations of 180° thanks to the advancement through meandering paths only with the perfect execution of the inchworm-like motion. In this way the risk to deform the body cavity from the inside, which cause pain and discomfort to the patient, is avoided.

Thanks to the quick process of the inchworm-like motion and the firm anchorage of the robot to the walls of the body cavity which is passed through, the robot can spread apart the walls while moving forward without blowing large amount of air in the cavity. In any case, the robot can clear its way by blowing air (FIG. 2C), but a limited amount of air at low relative pressure is anyway necessary, thereby reducing patient's discomfort.

The endoscopic robot according to the invention is highly versatile and can be used in many different endoscopic procedures. In addition, it can be used as a propelling member for devices to be inserted into the patient's body, such as a catheter.

Thanks to its features, the robot of the invention can be made at reduced cost both in a reusable form and in a partially or fully disposable form.

The robot of the invention may help in increasing the diffusion of the so-called minimally invasive surgery, thus considerably reducing discomfort and pain of the patients, the costs of surgical and/or diagnostic operations and the patient recovery time.

Further variations and/or modification can be made to the endoscopic robot according to the invention by a person skilled in the art to fulfill additional contingent needs, without departing from the scope of the invention as set forth in the appended claims.

We claim:

1. An elongated medical instrument defining a longitudinal axis along its length adapted for migration through a lumen of a tubular body part having an intraluminal wall comprising:

a distal section having distal means for engaging and disengaging the intraluminal wall of the tubular body part by selectively producing a pneumatic vacuum (V) between said distal section and the intraluminal wall;

said distal means comprising a front chamber (14) with first rigid walls (15), a first plurality of holes (16) passing through said first rigid walls (15) from said front chamber to said intraluminal wall and a first flexible aspirating tube (18) opening into said front chamber (14) and connected to fluid aspiration equipment outside a patient which delivers or aspirates a fluid from said front chamber;

a proximal section having proximal means for engaging and disengaging the intraluminal wall of the tubular body part by selectively producing a pneumatic vacuum (V) between said distal section and the intraluminal wall;

said proximal section comprising a back chamber (19) with second rigid walls (20) and a second plurality of holes (16) passing through said rigid walls (20) from said back chamber to said intraluminal wall and a second flexible aspirating tube (21) opening into said back chamber (19) and connected to said fluid aspiration equipment outside the patient which delivers or aspirates said fluid from said back chamber;

an intermediate section respectively abutting and engaging said distal section and said proximal section, said intermediate section being a single unitary resilient wall (5) defining an inner chamber (6), means for supplying and aspirating said fluid to and from said inner chamber to respectively expand said intermediate section along said longitudinal axis and permit contraction of said intermediate section to an original unexpanded form and means for selectively engaging and disengaging either said distal means or proximal means with the intraluminal wall so as to permit said intermediate section to effect migration of said distal, said intermediate and said proximal section through the lumen by supplying or aspirating said fluid to and from said inner chamber.

2. The elongated medical instrument according to claim 1, wherein said fluid is air.

3. The elongated medical instrument according to claim 1, wherein said wall (6) has a bellows structure.

4. The elongated medical instrument according to claim 1, wherein said wall (6) is made from a flexible material, wherein said intermediate section is able to be passively bent around a loop in the intraluminal wall through which said elongated medical instrument passes.

5. The elongated medical instrument according to claim 1, wherein said intermediate section comprises a single variable length segment (2) flexibly extending between said distal section and said proximal section.

6. The elongated medical instrument according to claim 1, wherein said inner chamber (6) is longitudinally crossed by a portion (26) of said first flexible aspirating tube (18), said portion (26) being shaped as an helical spiral to be elastically deformable.

7. The elongated medical instrument according to claim 1, wherein said intermediate section (2) has an elastic, deformable sheath (11) externally covering said wall.

8. The elongated medical instrument according to claim 1, wherein said first plurality of holes are positioned on said first rigid walls so as to permit the lumen to be spread apart by blowing said fluid through said first plurality of holes (16) of said distal section.

* * * * *